United States Patent [19]

Niedrach et al.

[11] Patent Number: 4,948,492
[45] Date of Patent: Aug. 14, 1990

[54] ELECTRODE PROBE FOR USE IN AQUEOUS ENVIRONMENTS OF HIGH TEMPERATURE AND HIGH RADIATION

[75] Inventors: Leonard W. Niedrach, Schenectady, N.Y.; Maurice E. Indig, Fremont, Calif.; Laura L. H. King, Raleigh, N.C.

[73] Assignee: General Electric Company, San Jose, Calif.

[21] Appl. No.: 345,740

[22] Filed: May 1, 1989

[51] Int. Cl.$^5$ ............................................. G01N 27/26
[52] U.S. Cl. ................................. 204/435; 376/245; 376/256
[58] Field of Search ................. 376/245, 256; 204/435

[56] References Cited

U.S. PATENT DOCUMENTS

| | | | |
|---|---|---|---|
| 4,636,292 | 1/1987 | Fejes et al. ........................... | 204/404 |
| 4,725,399 | 2/1988 | McCulloch et al. ................. | 376/247 |
| 4,759,902 | 7/1988 | Anstine ................................ | 376/306 |
| 4,882,122 | 11/1989 | Head et al. ........................... | 376/245 |

Primary Examiner—Harvey E. Behrend
Assistant Examiner—Nina Bhat
Attorney, Agent, or Firm—Robert R. Schroeder

[57] ABSTRACT

An electrode probe suited for employment as a reference electrode in a high pressure, high temperature, and high radiation field environment such as adjacent the core of a nuclear reactor is described. The electrode is a brazed and welded assembly consisting of only ceramic and metal parts including a sapphire crucible which is brazed to a kovar/stainless steel housing, welded in turn, to a coaxial cable assembly for signal transfer. The crucible incorporates an integrally formed pedestal through which a conductor wire extends and over which is positioned a selectively coated cylindrically shaped sealing retainer. The device is particularly suited for employment with a silver/silver chloride electrode system.

19 Claims, 2 Drawing Sheets

ELECTRODE PROBE FOR USE IN AQUEOUS ENVIRONMENTS OF HIGH TEMPERATURE AND HIGH RADIATION

BACKGROUND

The nuclear power industry long has been engaged in a multitude of studies and investigations seeking improvement in the stamina and reliability of the materials and components forming a reactor based power system. One such investigation has been concerned with intergranular stress corrosion cracking (IGSCC) which heretofore principally has been manifested in the water recirculation piping systems external to the radiation intense reactor core regions of nuclear facilities. Typically, the piping architecture of these external systems is formed of a stainless steel material. Generally, these studies have determined that three factors must occur in coincidence to create IGSCC promotional conditions. These factors are: (a) a sensitization of the metal (stainless steel) for example, such as caused by a chromium depletion at grain boundaries which may be caused by heat treatment in the course of normal processing of the material or by welding and the like procedures; (b) the presence of tensile stress in the material; and (c) the oxygenated normal water chemistry (NWC) environment typically present in a boiling water reactor (BWR). This latter environment is occasioned by any of a variety of oxidizing species contributed by impurities in reactor coolant water. By removing any one of these three factors, the IGSCC phenomenon is essentially obviated. Such removal particularly has been accomplished with respect to the latter, oxygenated environment factor, through employment of an electrochemical potential monitoring approach combined with an associated hydrogen water chemistry (HWC) technique providing for a controlled addition or injection of hydrogen into the aqueous coolant environment.

Electrochemical potential monitoring is carried out employing paired electrochemical half-cell probes or electrodes which are mounted within the recirculation piping or in an external vessel which has its water source from the reactor water in the recirculation piping. The electrodes are accessed to the external environment through gland type mountings or the like. Where, as in the instant application, the electrode system of interest involves the potential from a metal corrosion electrode, then the reference electrode can conveniently be a metal-insoluble salt electrode, if the metal salt couple is chemically stable and if appropriate thermodynamic data is available. Accordingly, one of the thus-mounted probes which is configured as a reference electrode may be based, for example, on a silver/silver chloride half-cell reaction. Once the reference electrode half-cell is defined, the cell is completed with the sensing cell portion based upon a metal such as platinum or stainless steel. Calibration of the reference electrode and/or the electrode pair is carried out by thermodynamic evaluation and appropriate Nernst based electrochemical calculations in combination with laboratory testing within a known environment.

Half cell electrodes developed for use in reactor recirculation piping traditionally have been configured with metal housings, high temperature ceramics, and polymeric seals such as Teflon. These structures have performed adequately in the more benign and essentially radiation-free environments of recirculation piping.

Over the recent past, investigators have sought to expand the electrochemical potential (ECP) monitoring procedures to the severe environment of the fluid in the vicinity of the reactor core itself for the purpose of studying or quantifying the effect of hydrogen-water chemistry adjustment in mitigating irradiation assisted stress corrosion cracking (IASCC) as well as IGSCC. Within the reactor core, the monitoring electrode can be mounted, for example, with otherwise unemployed or in tandem with the traveling instrumentation probe (TIP) of available local power range monitors (LPRM) and the like. The monitors are located in a severe, high temperature (typically 285° C.), high pressure and high radiation (typically $10^9$R (rads) per hour gamma, $10^{13}$R per hour neutron) environments. Probe structures of earlier designs are completely inadequate for this reactor core environment, both from a material standpoint and with respect to the critical need to prevent leakage of radioactive materials to the environment outside of the reactor vessel.

SUMMARY

The present invention is addressed to a reference electrode probe for evaluating electrochemical potentials and the like which has a robust structure particularly suiting it for employment within the rigorous environment of the reactor core of a nuclear power facility. Half cell electrode components are positioned within a single crystal alumina (sapphire) retainer or crucible. This sapphire crucible is structured having a base and sidewalls defining an internally-disposed cavity for retention of electrode-defining components. To achieve a highly reliable internal seal, a pedestal is integrally formed extending within the noted cavity from the crucible base and through which an access channel is formed. Electrical communication to the cavity retained components is provided by a conductor which is positioned within this channel. A cylinder with a cap coated with the metal component, i.e. silver, of the half cell is positioned over and intimately compressively bonded and sealed over the pedestal and is in electrical contact with the conductor to form the internal seal at a high level of integrity. For achieving a compatibility of thermal expansion, the sealing retainer is formed of kovar having appropriate sintered coatings thereon. The crucible is capped with a sapphire cap permitting diffusion communication with the aqueous environment within which the electrode is employed. A kovar transition member is sealed by appropriate silver brazing with the sapphire crucible to provide a second seal and this kovar sleeve is supported by a positioning and signal transfer arrangement including a stainless steel transition piece which, in turn, is sealed with a cable connector assembly.

As another feature, the invention provides an electrode for empolyment in monitoring the electrochemical potential of a body of fluid which includes an alumina cell retainer having a base region with an externally disposed surface attachment region and sidewalls extending to an access opening therefrom for defining an internally disposed cavity. The internal pedestal that extends within the cavity from the base of the retainer which has a continuous access channel extending through the base and the pedestal. A first metallic coating is intimately adhered to the externally disposed surfaces of the pedestal and a second metallic coating is intimately adhered to the base externally disposed surface attachment region. A metal salt electrochemical reactant is located within the cavity of the cell retainer and a sealing retainer, the surface of which is a select metal to define with the metal salt the components constituting a metal-metal salt electrode. The sealing retainer has a concave interior surface positioned over the pedestal and affixed thereto in an intimate sealed adjacency. A cap formed of alumina is positioned over the cell retainer opening for retaining the noted electrode components within the cavity while permitting electrolytic communication with the fluid. A sleeve arrangement is provided which is formed of a first select metal exhibiting a coefficient of expansion compatible with the alumina cell retainer and which has an acceptance portion for an intimately sealed braze connection with the outside diameter of the cell retainer. This sleeve arrangement has a first internal channel extending along its lengthwise extent. A first conductor is connected in electrical contact with the interior surface of the sealing retainer and insulatively extends therefrom through the first internal channel. A positioning and signal transfer arrangement is provided for operatively supporting the sleeve arrangement and for conveying electrical signals from the noted first conductor.

As another feature, the invention provides a reference electrode for employment within a fluid medium and having an electrode system involving a metal-metal ion couple. A cylindrically shaped alumina cell retainer is provided having a base region with an externally disposed surface attachment region and a cylindrical sidewall extending therefrom to an access opening to define an internally-disposed cavity. A cylindrically shaped, integrally formed pedestal extends within the cavity from the base region to a flat coupling surface and has a continuous access channel extending from the coupling surface through the base region. A first metallic coating is intimately adhered to externally disposed surfaces of the pedestal and a second metallic coating is intimately adhered to the base externally disposed surface attachment region. A sealing retainer, formed as a cylinder with a closed end, having a externally disposed silver coating, has an interior surface positioned over the pedestal in closely nesting adjacency and sealably fixed thereto. A silver chloride salt is located within the cavity for providing the component of a metal-salt electrode with silver coating of the retainer. A cap, formed of alumina and positioned over the cell retainer opening, provides for retaining the electrode components within the cavity while permitting electrode system communication with the fluid media. A sleeve arrangement, formed as a kovar cylinder and having an acceptance portion at one end thereof intimately sealed by brazed connection with the cell retainer second metallic coating is provided which has a first internal channel extending therethrough to an attachment surface. An elongate transition component, formed of stainless steel, having a second internal channel extending from a transition end to a sealing end is provided which is weldably connected at the transition end in fluid sealing relationship with the sleeve arrangement attachment surface. A cable connector assembly is provided having a metal collar which is weldably attached and sealed to the transition component sealing end and which has a first conductor extending therethrough for communication with the second internal channel. A second conductor is coupled with the first conductor and insulatively extends through the first channel, the second channel, and the continuous access channel for electrical contact with the sealing retainer interior surface.

Other objects of the invention will, in part, be obvious and will, in part, appear hereinafter.

The invention, accordingly, comprises the apparatus possessing the construction, combination of elements, and arrangement of parts which are exemplified in the following detailed disclosure. For a fuller understanding of the nature and objects of the invention, reference should be had to the following detailed description taken in connection with the accompanying drawings.

DETAILED DESCRIPTION

While having utility in a broad variety of industrial monitoring functions, the electrode structure of the instant invention finds particular utility operating under the rigorous environment of the reactor core of a nuclear power facility. No elastomeric seals or polymeric components are present in its structure which incorporates a sealing architecture of the highest integrity. In the latter regard, a brazed and welded assembly consisting only of ceramic and metal parts forms the structure of the device. The electrode finds preferable employment as a reference component of an electrode system involving a metal-metal ion couple and thus the instant electrode can conveniently be a metal slightly soluble salt electrode. For the embodiment shown, the device is a silver-silver chloride reference which functions reversibly. In general, these electrodes consist of a silver metal with silver chloride immersed in a solution containing chloride anions. The electrode reaction is:

$$AgCl(s) + e^- \rightarrow Ag(s) + Cl^-.$$

At 25° C., the collector chemical potential of such an electrode can be computed as:

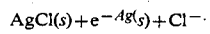
$$V(SHE) = 0.2222 - 0.05915 \log_{10} aCl^-.$$

V(SHE) means the voltage of the electrode of interest versus the standard hydrogen electrode. For a more detailed discussion in connection with the above, reference is made to "Physical Chemistry" by G. W. Castellan, Chapter 17, "Equilibria in Electrochemical Cells", pp 344–382, Addison-Wesley Publishing Co., Reading, Mass. (1964).

Figure 1:
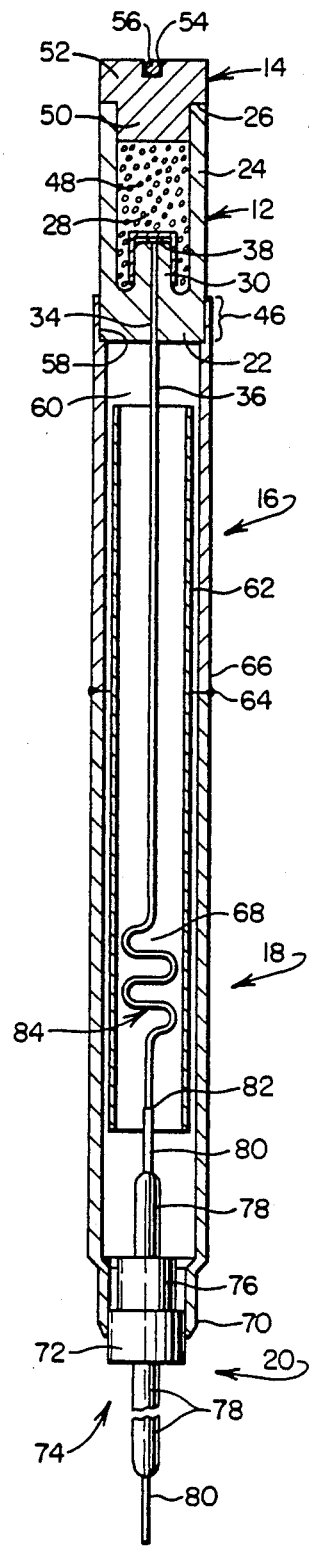
FIG. 1 is a sectional view of an electrode according to the invention.

Referring to FIG. 1, the structure of the reference electrode according to the invention is represented in general at 10 in sectional fastion. Probe 10 has a generally cylindrical structure comprised of five principal components including a cylindrically shaped cell retainer or crucible 12; a cylindrical cap formed over crucible 12 at 14, and a positioning and transfer arrangement which includes: a crucible sleeve 16; an elongate cylindrical transition component or piece 18; and a cable assembly or connector 20.

Retainer or crucible 12 is structured not only to withstand the duress otherwise imposed by radiation, high temperatures, and pressure, but also to achieve a highly reliable seal to avoid the incursion of reactor coolant water through the electrode and ultimately to the outside environment. The crucible, in its preferred embodiment, is formed of sapphire which is a single crystalline form of alumina. The sapphire material, not only provides a requisite electrical insulation but also, by virtue of its single crystalline structure, is highly resistant to attack by the universal solvent water within which it is immersed and, importantly, exhibits no grain boundaries. Thus, there is no integranular penetration into the material even though there will be some general corrosion attack. Accordingly, the material forming the crucible 12 is ideal for the contemplated environment. Other materials will occur to those art skilled, for example high purity alumina or ruby. Retainer 12 is formed having a cylindrical base region 22 from which a cylindrically shaped wall 24 extends to an end surface or access opening 26. The walls 24 define an internally-disposed cavity 28 within which there is an integrally formed upstanding cylindrical pedestal 30.

Figure 2:
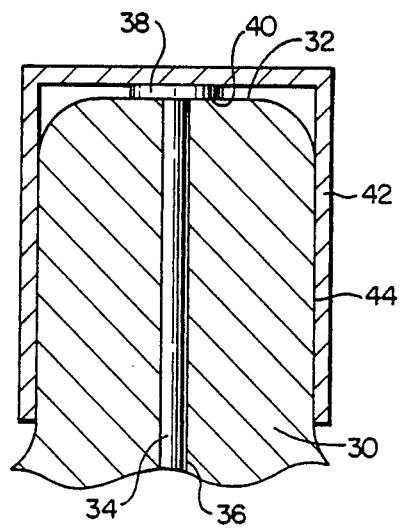
FIG. 2 is a partial sectional view of a sealing retainer structure shown in FIG. 1.

Referring additionally to FIG. 2, pedestal 30 is seen to extend within the cavity 28 from the base region 22 to a flat coupling surface 32. A cylindrical bore or continuous access channel 34 extends from the coupling surface 32 and through base region 22. Channel 34 serves to provide access for an electrically conductive transmission line or conductor wire 36 which may be formed of kovar and flattened at its end position 38 in disk shaped fashion. Wire 36 is seen to be inserted through the channel 34 and the inward side 40 of the disk 38 is shown in abutting contacting adjacency with the coupling surface 32. Kovar materials are a group of alloys, e.g. Fe 53.8%, Ni 29%, Co 17%, and Mn 0.2% which exhibit a coefficient of thermal expansion characteristic compatible with that of the alumina materials of the retainer or crucible 12. Preferably, the disk shaped head 38 is nickel plated and then sanded.

The first of the internal seals for electrode 10 is developed with respect to the necessary electrical communication provided by rod 36 through the employment of pedestal 30 in conjunction with a sealing retainer or post cap 42 which also is fashioned of kovar. Retainer 42 formed as a cylinder having a closed end and exhibiting an internal diameter serving to provide an outwardly disposed seal at its union with the lateral surface 44 of pedestal 30. To achieve a sealed union of high integrity between the concave internal surface of cap 42 and outer surface of pedestal 30, certain metallurgical procedures are carried out. In this regard, the surface of pedestal 30 is metallized by painting it with a tungsten paint, following which it is inspected and then fired employing conventional procedures. The fired surface then is inspected and the thus-metallized region is nickel-plated, following which the thus-metallized regions are nickel-plated and sintered. The sintered surface then is inspected, following which it is silver-plated.

The kovar cap 42 also is subjected to a somewhat elaborate procedure of surface treatment in view of its presence within a silver chloride environment, which is a strong oxidizing agent. It also will be observed that the ultimate coating is silver which forms part of the electrode system. In preparation of this machined cup-like part, it first is cleaned and inspected, following which it undergoes a post-machine annealing procedure and is then nickel-plated. The nickel-plated cup-like structure is sintered to improve the plating bond, whereupon the sintered part is again inspected. A second nickel plating and sintering procedure then is carried out following which the part again is inspected. A nickel strike procdure then is carried out, following which the part is plated with rhodium and the thus-plated cap then is sintered and inspected. The rhodium plating and sintering steps again are carried out, following by a subsequent inspection. A rhodium plating arrangement is provided, inasmuch as rhodium is very non-reactive. The inspections are required to assure continuity of the separate platings.

The component 42 then is silver-plated and the silver-plating is sintered following which an inspection procedure takes place. The device 42 again is silver-plated as a last step in its treatment. In the assembly of this sealing arrangement, the disk component 38 of conductor 34 is spot welded to the underside of the top surface of cap 42. Additionally, the cap 42 is sealably attached to the surface of pedestal 30 by silver brazing. Additional amounts of silver braze may be applied during brazing to provide a thicker coating of silver on the retainer cap and also may fill the gap between pedestal 30 and cylinder wall 44.

Returning to FIG. 1, the lower, outer cylindrical surface portion of base region 22 of the crucible 12 is a surface attachment region, the extent of which is represented by bracket 46. This region also is metallized in the same manner as the surface of pedestal 30 in order to provide a next seal in the electrode architecture.

Shown positioned within cavity 28 of the retainer 12 is a slug of silver chloride which herein is shown schematically in granular form as an aqueous suspension as represented at 48. In a preferred arrangement, the silver chloride may be melted and formed into rods, portions or plugs of which then may be located within cavity 28.

The end cap 14 also is formed of sapphire, the single crystal form of alumina and may, for example, be fashioned of the noted alternate materials. Cylindrical in general form, the cap 14 is seen having a neck component 50 which is integrally formed with a top flange region 52. The cap is dimensioned so as to provide a "tight" fit over access opening 26 and with the cylindrical interior surface of the cavity 28. The noted fit of the cap 14 to the retainer or crucible 12 is one which permits electrolytic communication with the reactor coolant water with a very minimum movement or mass transfer of water or material. In effect, a diffusion junction is formed between cap 14 and walls 24 of the container. Exemplary of the type of fit involved, the access opening diameter at crucible 12 may, for example, be machined to provide a diameter of 0.235 inch with a tolerance of +0.001, −0.000, while the corresponding diameter of the neck component 50 at cap 14 may be machined with a diameter of 0.235 inch under tolerances of +0.00, −0.001 inch. Further retention of the cap 14 is provided by a transverse slot 54 within which a stainless steel wire, shown in section at 56, is positioned thereabout in harness fashion and attached at the lower connector 20 region of device 10.

The crucible or retainer 12 of device 10 is initially supported by the cylindrical crucible sleeve 16 which, to achieve compatibility with sapphire crucible 12 from the standpoint of the thermal coefficient of expansion thereof, is formed also of kovar. Note that the internal diameter of the sleeve 16 is offset, for example, by counterboring at 58 to provide an acceptance portion suited for receiving and being attached to the surface attachment region 46 of base region 22 of crucible 12 for forming an intimate seal thereat. The initially produced cylinder of kovar for sleeve 16 is prepared by initially cleaning and inspecting it, following which a post machine annealing procedure is carried out. Following this annealing procedure, the component is nickel-plated and that nickel-plating and sintering following which it is inspected. A second nickel-plating and, sintering procedure then is carried out, followed by a next inspection. Generally, the thus-prepared component is stored in sealed plastic packaging until it is utilized. Attachment developing an intimate seal of the surface attachment region 46 of crucible 12 with the acceptance portion 58 of sleeve 16 is provided by silver brazing. This arrangement then completes a highly secure second seal for the electrode 10 as is required in view of the intended use thereof within the port region of a reactor. The hollow interior 60 of cylindrical (annular) sleeve 16 provides an internal channel through which the wire or conduit 36 may pass. To assure that the wire 36 is insulated from the internal surfaces of sleeve 16, an alumina tube 62 is inserted within channel 60. Annular ceramic tube 62 provides such insulation while remaining immune from the temperatures encountered with the intended use of device 10.

Kovar sleeve 16 is supported, in turn, by attachment to the cylindrical transition component 18 which, for the instant application may be formed of a type 304 stainless steel. The transition piece 18 is of corresponding diametric extent as sleeve 16 and is attached at its transition end 64 to the corresponding attachment surface 66 thereof utilizing a tungsten inert gas weld (TIG) as applied, for example, by a tube welder. The hollow interior 68 of transition tube 18 provides an internal channel representing a continuation of the channel 60 of sleeve 16. Alumina tube 62 is seen to extend continuously thereinto. The lower end of transition tube 18 is formed in necked down fashion to provide a sealing end 70. End 70 is welded by the noted tungsten inert gas welding technique to the cylindrical stainless steel collar 72 of a cable connector assembly represented generally at 74 and which is shown having a ceramic support component 76 through which a mineral insulated cable 78 extends. Cable 78 may be provided having a stainless steel outer shell within which the noted mineral insulation may be provided as alumina and centrally disposed within which is a conducting cable 80. The mineral insulated cable 78 extends outwardly to the ambient environment from the reactor environment region in the application of interest. To provide an electric circuit completing connection with the lead 80, kovar conductor 36 is spot welded thereto at 82. To facilitate this attachment and provide a modicum of tension within the kovar conductor 36, a spring winding is formed in conductor 36 as represented in general at 84. Cable assembly 74 is marketed, for example, by Reutor-Stokes, a division of General Electric Company, Twinsburg, Ohio.

Figure 3:
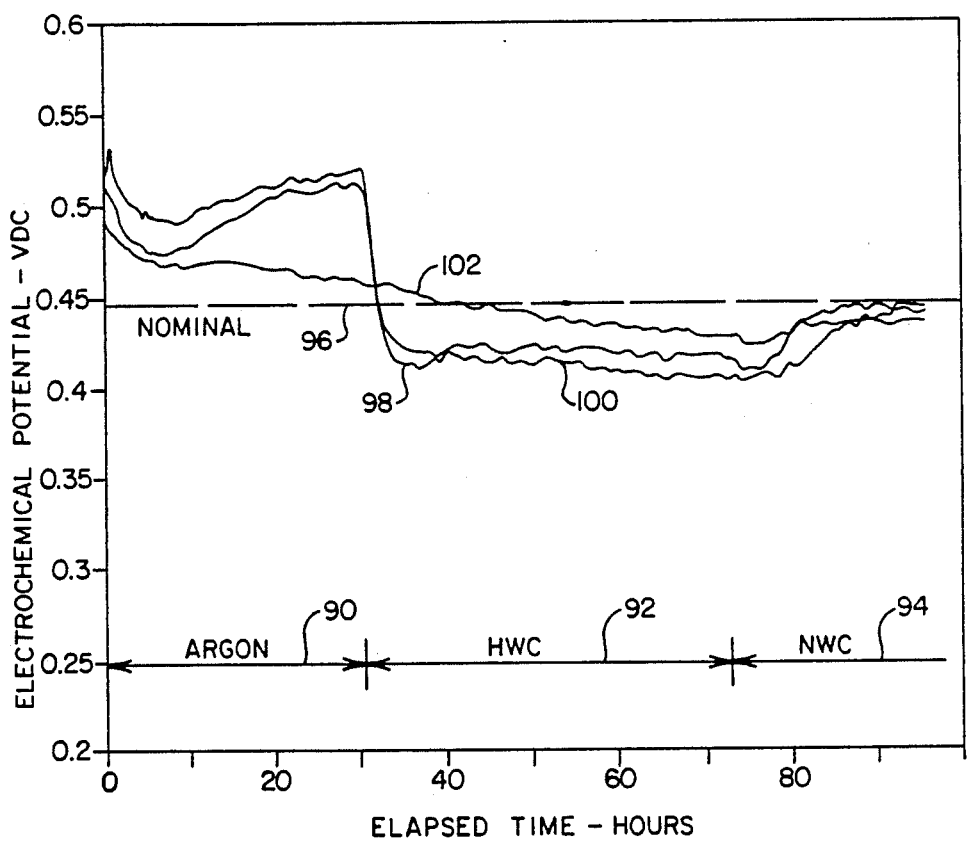
FIG. 3 is a graph showing a laboratory evaluation of an electrode according to the invention in conjunction with a standard electrode.

Referring to FIG. 3, a reference electrode fabricated in accordance with the teachings of the invention was subjected to a laboratory-based calibration check-out within an aqueous medium. This medium was provided by an autoclave within which temperature and water chemistry are controlled. The test was carried out at a water temperature of 274° C. and in conjunction with a sequence of aqueous media conditions wherein certain dissolved gases were introduced. A first such dissolved gas was argon, as labeled along the elapsed time portion of the figure as represented at 90. The aqueous media then was subjected to hydrogen water chemistry as represented by the interval 92 which provided for the injection of hydrogen. Finally, the aqueous medium was subjected to a normal boiling water chemical (NWC) as represented at 94 which was provided by injection of oxygen. A nominal or theoretical value for electrochemical potential was computed from thermodynamics and is represented by the horizontal line identified as "Nominal" at 96. The voltage from each test electrode was measured against the reference, a copper/cuprous oxide/zirconium electrode. The voltage outputs in the different fluid media are shown as 98, 100, and 102. These voltage outputs are compared to the theoretical value, 96, to determine acceptablility of each test electrode. It may be observed from the figure that, following about a 30 hour break-in period, the electrodes of the invention performed satisfactorily and in concert with the theoretical potential.

Since certain changes may be made in the above-described apparatus without departing from the scope of the inventin herein involved, it is intended that all matter contained in the description thereof or shown in the accompanying drawings shall be interpreted as illustrative and not in a limiting sense.

We claim:

1. A reference electrode probe for employment in monitoring electrochemical potentials, comprising:

an alumina cell retainer having a base region with an externally disposed surface attachment region and sidewalls extending to an access opening therefrom for defining an internally disposed cavity, an integrally formed pedestal extending within said cavity from said base and having a continuous access channel extending through said base and said pedestal;

a metal salt electrochemical reactant located within said cavity;

a sealing retainer, the surface of which is a select metal to define with said metal salt the components consituting a metal-metal salt electrode, located within said cavity and having an interior surface positioned over said pedestal and affixed thereto in intimate sealed adjacency;

a cap formed of alumina and positioned over said cell retainer access opening for retaining said electrode components within said cavity while permitting electrolytic communication with said cavity;

an annular sleeve formed of a first select metal exhibiting a coefficient of expansion compatible with said alumina cell retainer and having an acceptance portion for intimately sealed brazed connection with said cell retainer surface attachment region and having a first internal channel extending along the lengthwise extent thereof;

a first electrical conductor connected in electrical contact with said interior surface of said sealing retainer and insulatively extending therefrom through said first internal channel; and positioning and signal transfer means for operatively supporting said sleeve means and conveying electrical signals from said first conductor.

2. The electrode probe of claim 1 in which said positioning and signal transfer means comprises:

a transition component formed of a second select metal and having a second internal channel extending therethrough to a sealing end and sealably connected with said sleeve means;

said first conductor extending into said second internal channel; and cable connector means having a collar weldably attached and sealed to said transition component sealing end and having a second conductor extending therethrough for connection with said first conductor.

3. The electrode probe of claim 1 in which said alumina cell retainer is formed from a single crystal sapphire.

4. The electrode probe of claim 1 in which said sealing retainer is formed of kovar the surface of which is an intimately adhered coating of said electrode metal.

5. The electrode probe of claim 1 in which said first conductor includes an integrally formed disk positioned upon said pedestal over said access channel and electrically coupled with said sealing retainer interior surface.

6. The electrode probe of claim 1 in which said sleeve means is formed of kovar.

7. The electrode probe of claim 6 in which said transistion component is formed of stainless steel and is welded to said sleeve means to form a continuous internal channel from said first and second internal channels.

8. The electrode of claim 7 including an elongate annular alumina insulator located within said continuous internal channel for electrically insulating said first conductor.

9. The electrode of claim 1 in which said first conductor is kovar wire.

10. A reference electrode probe comprising:
a cylindrically shaped alumina cell retainer having a base region with an externally disposed surface attachment region and a cylindrical sidewall extending therefrom to an access opening to define an internally disposed cavity, a cylindrically shaped, integrally formed pedestal extending within said cavity from said base region to a flat coupling surface and having a continuous access channel extending from said coupling surface through said base region, a first metallic coating intimately adhered to the externally disposed surface of said pedestal, a second metallic coating intimately adhered to said base region externally disposed surface attachment region;
a sealing retainer, formed as a cylinder with a closed end, having an externally disposed silver coating, and having an interior surface positioned over said pedestal in closely nesting adjacency and sealably fixed thereto;
silver chloride salt located within said cavity for providing, with said retainer silver coating the components of a metal-salt electrode;
a cap formed of alumina and positioned over said cell retainer opening for retaining said electrode components within said cavity while permitting electrode communication;
a kovar annular cylindrical sleeve having an acceptance portion at one end thereof intimately sealed by brazed connection with said cell retainer second metallic coating, and having a first internal channel extending therethrough to an attachment surface;
a stainless steel annular cylindrical transition component having a second internal channel extending from a transition end to a sealing end and weldably connected at said transition end in fluid sealing relationship with said sleeve means attachment surface;
a cable connector having a metal collar weldably attached and sealed to said transition component sealing end and having a first electrical conductor extending therethrough for communication with said second internal channel; and
a second electrical conductor coupled with said first electrical conductor and insulatively extending through said first channel, second channel and said continuous access channel for electrical contact with said sealing retainer interior surface.

11. The reference electrode probe of claim 10 in which said alumina cell retainer is single crystal sapphire.

12. The reference electrode probe of claim 10 in which said sealing retainer is formed of kovar metal, the surface of which is covered with a sequence of coatings including sintered nickel plate, sintered rhodium plate, ans sintered silver plate.

13. The reference electrode probe of claim 12 in which said pedestal first metallic coating is provided as a sequence of coatings including a fired, metalized surface which is covered with a sintered nickel plate over which is formed a sintered silver plate.

14. The reference electrode probe of claim 13 in which said sealing retainer is fixed to said pedestal with a silver braze.

15. The reference electrode probe of claim 10 in which said second conductor includes an integrally formed disk positioned upon said pedestal flat coupling surface over said access channel and weldably coupled to said sealing retainer interior surface.

16. The reference electrode probe of claim 10 including an annular alumina tube located within said first and second channels through which said second conductor extends for effecting the insulation thereof.

17. The reference electrode probe of claim 10 in which said alumina cell retainer externally disposed surface attachment region is nestably positioned within said sleeve means acceptance portion and is sealed thereto with a silver braze.

18. The reference electrode probe of claim 10 in which said alumina cell retainer externally disposed attachment region second metallic coating is provided as a sequence of coatings including a fired, metalized surface coating which is covered with a sintered nickel plate, over which is formed a sintered silver plate.

19. The reference electrode probe of claim 10 in which said sleeve means is covered with a sintered nickel plate coating.

* * * * *